United States Patent
Karell

Patent Number: 5,284,161
Date of Patent: Feb. 8, 1994

[54] SNOPPER-THE SNORING STOPPER ANTI-SNORING MOUTH DEVICE

[76] Inventor: Manuel L. Karell, 3573-22 St., San Francisco, Calif. 94114

[21] Appl. No.: 975,425

[22] Filed: Nov. 12, 1992

[51] Int. Cl.$^5$ ............................................. A61F 5/56
[52] U.S. Cl. .................................. 128/848; 128/741; 607/134
[58] Field of Search ............... 128/741, 419 R, 420 R, 128/420 A, 421, 422, 423 R, 783, 784, 787, 848

[56] References Cited

U.S. PATENT DOCUMENTS

| | | | |
|---|---|---|---|
| 3,480,010 | 6/1969 | Crossley | 128/132 |
| 4,519,400 | 5/1985 | Brenman et al. | 128/421 |
| 4,644,330 | 2/1987 | Dowling | 340/575 |
| 4,669,459 | 6/1987 | Spiewak | 128/136 |
| 4,788,533 | 11/1988 | Mequignon | 340/575 |
| 4,901,737 | 2/1990 | Toone | 128/861 |
| 4,924,880 | 5/1990 | O'Neill et al. | 128/419 R |
| 4,944,310 | 7/1990 | Sullivan | 128/848 |
| 5,042,506 | 8/1991 | Liberati | 128/848 |
| 5,190,053 | 3/1993 | Meer | 128/787 |

FOREIGN PATENT DOCUMENTS 1553140  3/1990  U.S.S.R. .............................. 128/787

OTHER PUBLICATIONS

Herbert Paskow, DDS—Dentistry's Role in Treating Sleep Apnea and Snoring—NJ Medicine vol. 88–No. 11 Nov. 1991, pp. 815-817.

*Primary Examiner*—William E. Kamm
*Assistant Examiner*—Marianne Parker

[57] ABSTRACT

A novel medical device, SNOPPER—The Snoring Stopper TM anti-snoring mouth device, is inserted into the mouth. The device comprises a denture-like(10) apparatus for supporting electrodes(12) in such a manner that the electrodes make contact with the roof of the mouth. Electrical stimulation induces contraction of relaxed muscles, thereby preventing or stopping snoring. Electrical energy is provided to the device via wires for connection to an external stimulator(16) or via a self-contained, battery-powered, microminiturized electronic stimulator(20). Stimulation can be constant or intermittent. Wave shape, amplitutde, length, and frequency is controlled by the individual for comfort and is automatically induced via a feedback mechanism.

4 Claims, 3 Drawing Sheets

SNOPPER-THE SNORING STOPPER ANTI-SNORING MOUTH DEVICE

BACKGROUND

1. Field of Invention

This invention generally relates to medical devices, and more particularly to a novel device inserted into the mouth to prevent or stop snoring.

2. Description of Prior Art

Snoring is caused, in part, by relaxation of muscles during respiration while asleep. Various devices have been introduced to alleviate snoring. One device (U.S. Pat. No. 4,669,459 to Spiewak, 1987) provides pressure to the muscles, and another (U.S. Pat. No. 4,901,737 to Toone, 1990) provides an open mouth position. Other devices attempt to keep the tongue protruded, for example, the Samelson and Gardy devices, *NJ Medicine*, Vol. 88 No. 11 Nov. 1991. Still other devices (such as U.S. Pat. No. 4,644,330 to Dowling, 1987 and U.S. Pat. No. 4,788,533 to Mequignon, 1988) attempt to stop snoring by sound feedback. One device, U.S. Pat. No. 3,480,010 to Crossley, 1969) provides electrodes that attach to the skin of the neck via a neck band to shock the sleeper and condition him against snoring. One device, (U.S. Pat. No. 5,042,506 to Liberati, 1991) attempts to train the muscles to prevent snoring. Continuous positive air pressure breathing devices (U.S. Pat. No. 4,944,310 to Sullivan, 1990) and surgery are currently used to treat severe snoring and obstructive sleep apnea.

OBJECTS AND ADVANTAGES

SNOPPER—The Snoring Stopper TM anti-snoring mouth device provides electrical stimulation to the muscles of the mouth, from inside the mouth, to induce contraction and tension of relaxed muscles, thereby eliminating snoring.

SNOPPER—The Snoring Stopper TM anti-snoring mouth device allows for direct action to the muscles. There is no need for retraining of muscles, sound feedback, sleep interruption, or abnormal mouth positions or tongue protrusion positions.

SNOPPER—The Snoring Stopper TM anti-snoring mouth device obviates the need for continuous positive air pressure breathing devices or surgery.

SNOPPER—The Snoring Stopper TM anti-snoring mouth device can be configured as a self-contained battery-powered system that delivers electrical stimulation that can be adjusted for individual comfort.

DESCRIPTION OF FIGS. 1-3

Figure 1:
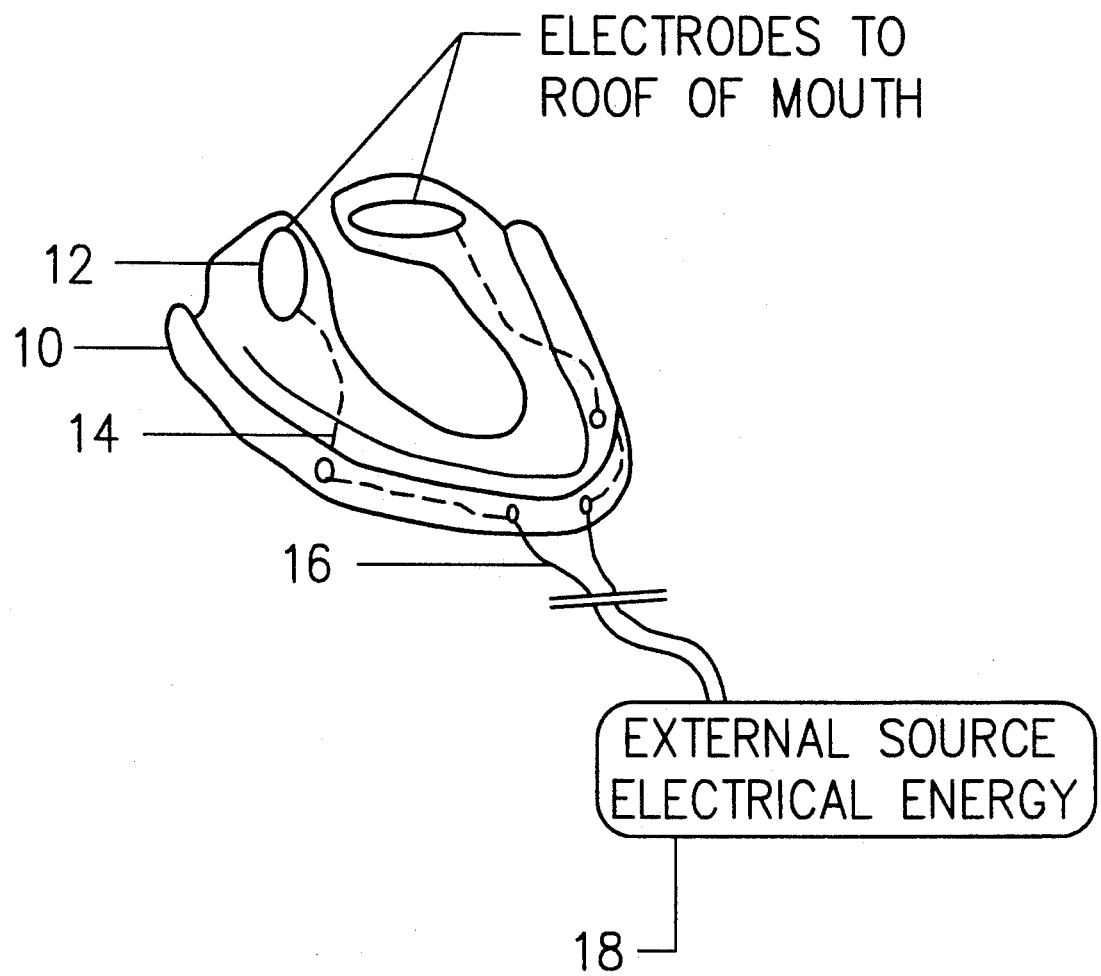
FIG. 1 is a perspective drawing of a SNOPPER—The Snoring Stopper TM anti-snoring mouth device
Figure 2:
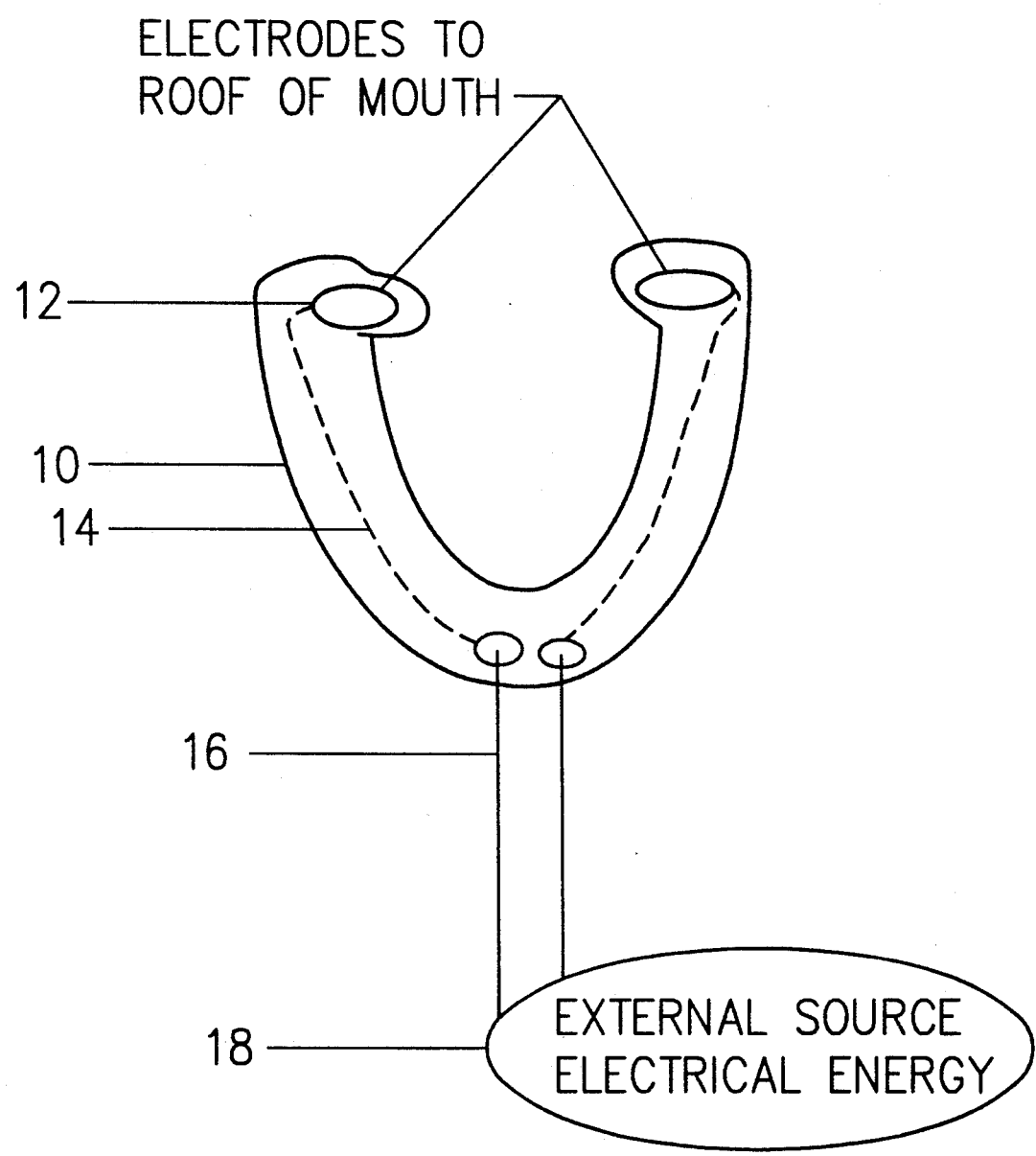
FIG. 2 is a plan view drawing of SNOPPER—The Snoring Stopper TM anti-snoring mouth device

A typical embodiment of my invention SNOPPER—The Snoring Stopper TM anti-snoring mouth device is illustrated FIG. 1 (perspective view) and FIG. 2 (plan view). Electrodes(12), which are supported by a molded denture-like device(10), make contact with the roof of the mouth. The electrodes(12) are connected to internal wires(14), which are connected to external wires(16). The external wires(16) are connected to an external source of energy(18).

Figure 3:
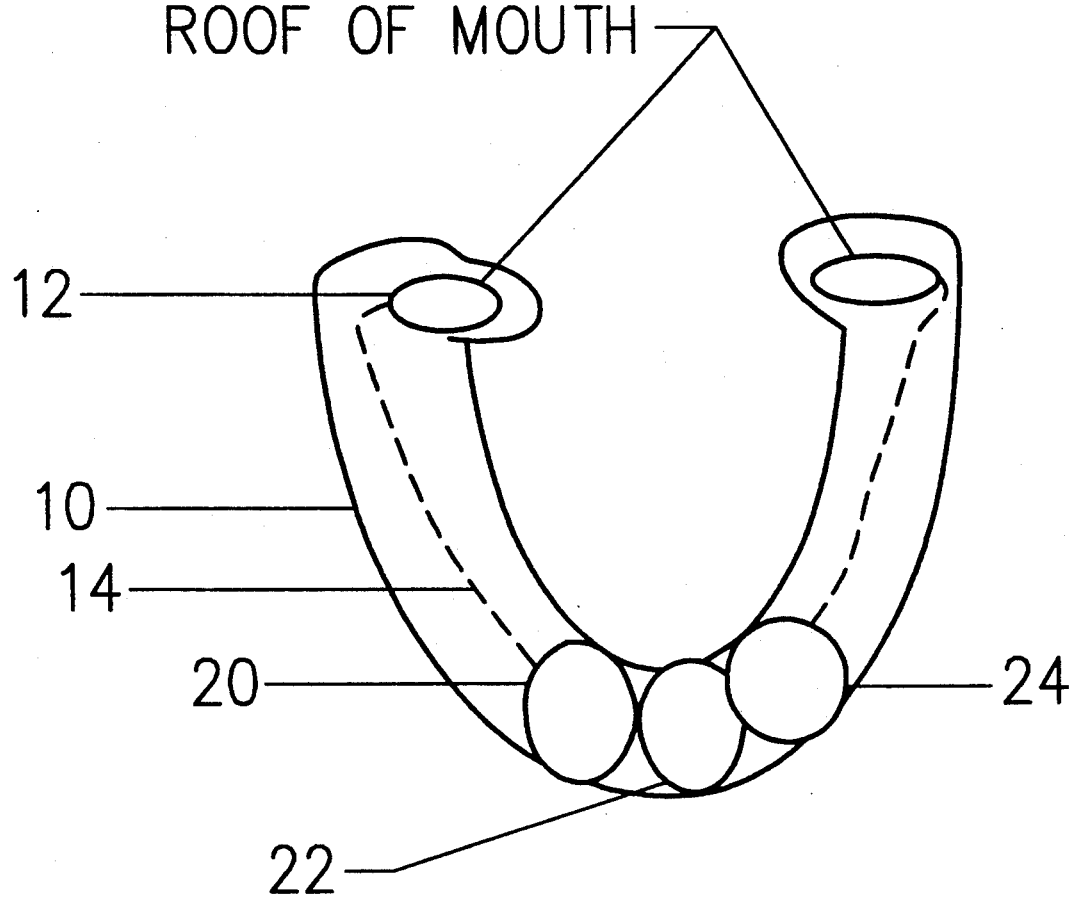
FIG. 3 is a plan view of an embodiment of SNOPPER—The Snoring Stopper TM anti-snoring mouth device with self-contained, battery-powered, microminiturized electronic stimulator

The plan view in FIG. 3 shows the device(10) alternatively constructed so that the internal wires(14), are in turn connected to a battery-powered(24), switched(22), microminiturized electronic stimulator unit(20).

OPERATION OF INVENTION

It is believed that snoring is caused, in part, by the relaxation of muscles during respiration while asleep. My SNOPPER—The Snoring Stopper TM anti-snoring mouth device, provides energized electrodes for delivering electrical stimulation. This stimulation induces contraction and tension of relaxed muscles thereby preventing or stopping snoring.

Electrical energy(18) is delivered to device(10) via external wires(16), transferred via internal wires(14) to electrodes(12). The energized electrodes induce contraction of muscles. Also, the electrical stimulation can induce rhythmic contraction waves that interfere with snoring rhythms. The device can be configured with a feedback mechanism (not shown) whereby snoring causes the onset of electrical stimulation.

Electrical energy can be provided via commercial transcutaneous electric nerve stimulator units (such as U.S. Pat. No. 4,949,721 to Toriu, 1990, or, U.S. Pat. No. 5,072,710 to Lee, 1991) attached to the wires(16). Alternatively, electrical energy can be provided via self-contained, battery-powered, microminiturized stimulator units within SNOPPER—The Snoring Stopper TM anti-snoring mouth device (FIG. 3); in this case, the device user controls and adjusts wave shape, amplitude, length, and frequency of the electrical stimulation, which can be intermittent or constant.

SUMMARY

SNOPPER—The Snoring Stopper TM anti-snoring mouth device with built-in electrodes is inserted into the mouth for electromuscular stimulation, inducing muscle contraction and tension, thereby preventing or stopping snoring. Electrical stimulation can be provided via connections to external source or via a self-contained, battery-powered, microminiturized electronic unit. Electrical stimulation can be constant or intermittent, using a variety of wave forms, amplitude, length, and frequency as required for individual comfort. The device itself and its electrodes can be made in a variety of shapes and materials.

Conclusions, Ramifications and Scope of Invention

The novel use of electrodes within a denture-like plate or other apparatus makes a SNOPPER—The Snoring Stopper TM anti-snoring mouth device beneficial. While the above description contains many specificities, these should not be construed as limitations on the scope of the invention, but rather as an exemplification of two preferred embodiments thereof. Many other variations are possible. For example, electrodes could be installed permanently through or between the teeth, or stimulation in this area can be prolonged to induce a beneficial long term hypotensive response. Accordingly, the scope of the invention should be determined not by the embodiments illustrated, but by the appended claims and their legal equivalents.

I claim:

1. An apparatus for the cessation of snoring, wherein said apparatus comprises:
   mouthpiece means for fitting over an entire upper tooth plate in a person's mouth and providing surfaces for contacting a upper mouth roof;
   electrode means, implanted within said mouthpiece means, for ceasing snoring through an application of electrical energy to the upper mouth roof; and
   energy means for supplying electrical energy to said electrode means.

2. An apparatus of claim 1, wherein said energy means is a microminiaturized stimulation unit implanted within said mouthpiece.

3. An apparatus of claim 1, wherein said electrode means is constructed of a soft, pliable, electroconductive rubber-like material.

4. An apparatus of claim 1, wherein said energy means comprises:
   internal wires implanted within said mouthpiece;
   external wires connected to said internal wires; and
   an external energy source connected to said external wires.

* * * * *